(12) United States Patent
Chan et al.

(10) Patent No.: US 12,008,688 B2
(45) Date of Patent: Jun. 11, 2024

(54) METHOD AND ELECTRIC DEVICE FOR PROCESSING BREAST TOMOSYNTHESIS IMAGES (71) Applicant: INSTITUTE FOR INFORMATION INDUSTRY, Taipei (TW)

(72) Inventors: Kai-Hsuan Chan, Taipei (TW); Yao-Min Huang, Taipei (TW)

(73) Assignee: INSTITUTE FOR INFORMATION INDUSTRY, Taipei (TW)

( * ) Notice: Subject to any disclaimer, the term of this patent is extended or adjusted under 35 U.S.C. 154(b) by 382 days.

(21) Appl. No.: 17/446,457

(22) Filed: Aug. 30, 2021

(65) Prior Publication Data

US 2023/0032486 A1 Feb. 2, 2023

(30) Foreign Application Priority Data

Jul. 21, 2021 (TW) .................................. 110126840

(51) Int. Cl.
| | |
|---|---|
| *G06T 11/00* | (2006.01) |
| *A61B 6/02* | (2006.01) |
| *A61B 6/50* | (2024.01) |
| *G06F 18/213* | (2023.01) |
| *G06N 3/04* | (2023.01) |
| *G06T 7/00* | (2017.01) |
| *G16H 30/20* | (2018.01) |

(Continued)

(52) U.S. Cl.
CPC ............ *G06T 11/003* (2013.01); *A61B 6/025* (2013.01); *A61B 6/502* (2013.01); *G06F 18/213* (2023.01); *G06N 3/04* (2013.01); *G06T 7/0012* (2013.01); *G16H 30/20* (2018.01); *G16H 30/40* (2018.01); *G16H 50/20* (2018.01); *G06T 2207/10112* (2013.01); *G06T 2207/20081* (2013.01); *G06T 2207/20084* (2013.01); *G06T 2207/30068* (2013.01)

(58) Field of Classification Search
CPC ................. G06T 11/003; G06T 7/0012; G06T 2207/20081; G06T 2207/20084; G06T 2207/30068; A61B 6/025; A61B 6/502; G06F 18/213; G16H 30/20; G16H 30/40; G16H 50/20
See application file for complete search history.

(56) References Cited

U.S. PATENT DOCUMENTS 11,145,056 B2 * 10/2021 Chan ..................... A61B 5/7485
2019/0130562 A1 * 5/2019 Liu ......................... G06V 20/64

(Continued)

*Primary Examiner* — Diane D Mizrahi
(74) *Attorney, Agent, or Firm* — CKC & Partners Co., LLC (57) ABSTRACT

A method for processing breast tomosynthesis images includes: obtaining multiple breast images, performing binarization operation and pooling operation to at least one marked breast image to obtain a lesion mask; training a convolutional neural network (CNN) according to the breast images and the lesion mask; obtaining multiple cropped images from the breast images of different layers according to a particular two-dimensional position, and inputting each cropped image into the CNN to obtain cropped heat maps; inputting the cropped heat maps into a recurrent neural network (RNN) in an order of the levels to obtain output heat maps, and combining the output heat maps to obtain a integrated heat map, and training the RNN according to the integrated heat map and the lesion mask.

12 Claims, 6 Drawing Sheets

(51) Int. Cl.
 *G16H 30/40* (2018.01)
 *G16H 50/20* (2018.01)

(56) References Cited

U.S. PATENT DOCUMENTS

2021/0019880 A1    1/2021  Chan
2021/0133954 A1*   5/2021  Melamed ............... G06N 20/00

* cited by examiner

METHOD AND ELECTRIC DEVICE FOR PROCESSING BREAST TOMOSYNTHESIS IMAGES

RELATED APPLICATIONS

This application claims priority to Taiwan Application Serial Number 110126840 filed Jul. 21, 2021, which is herein incorporated by reference.

BACKGROUND

Field of Invention

The present invention relates to a method for processing tomosynthesis images by combining images at different levels to detect a lesion.

Description of Related Art

Mammography examination technology mainly uses low-dose X-rays to examine human breasts. It can detect lesions such as lumps and calcification points. This technology can find the type and location of breast lesions more accurately than manual palpation. Therefore, mammography imaging is important in the detection of early breast cancer. Digital Breast Tomosynthesis (DBT) images include information in three-dimensional space, so the number of the images is tens of times higher than that of traditional two-dimensional mammography. If only two-dimensional deep learning models are used for detection, false positives will increase. This problem requires a deep learning method that can use neighboring three-dimensional information.

SUMMARY

Embodiments of the present disclosure provide a method for processing breast tomosynthesis images on an electrical device. The method includes: obtaining multiple breast images at multiple levels and performing a binarization operation and a pooling operation to at least one marked breast image of the breast images to generate at least one lesion mask; training a convolutional neural network according to the breast images and the at least one lesion mask, in which the convolutional neural network includes a first branch and a second branch, the first branch is configured to output at least one value to indicate whether a lesion exists, the second branch is configured to output a heat map, and loss values between the heat map and the at least one lesion mask are configured to train the convolutional neural network; obtaining multiple cropped images from the breast images at different levels according to a particular two-dimensional position, and inputting each of the cropped images into the convolutional neural network to obtain multiple cropped heat maps; and inputting the cropped heat maps into a recurrent neural network in an order of the levels to obtain multiple output heat maps, combining the output heat maps to obtain a first integrated heat map, and training the recurrent neural network according to loss values between the first integrated heat map and the at least one lesion mask.

In some embodiments, the convolutional neural network includes multiple first convolution layers. The first branch and the second branch follow the first convolution layers. The first branch includes a global average pooling layer and a fully connected layer. The second branch includes a second convolution layer which does not include the global average pooling layer and the fully connected layer.

In some embodiments, the method further includes: inputting multiple negative samples into the convolutional neural network, and retraining the convolutional neural network according to the negative samples that are determined to be positive.

In some embodiments, the recurrent neural network is a long short-term memory (LSTM) network.

In some embodiments, the first integrated heat map is an average of the output heat maps.

In some embodiments, the first integrated heat map corresponds to a first angle, a second integrated heat map corresponds to a second angle. The method further includes: combining the first integrated heat map and the second integrated heat map to generate a lesion position.

From another aspect, embodiments of the present disclosure provide an electrical device including a memory and a processor. The memory stores instructions. The processor is communicatively connected to the memory and configured to execute the instructions. The processor obtains multiple breast images at multiple levels and performs a binarization operation and a pooling operation to at least one marked breast image of the breast images to generate at least one lesion mask. The processor is also configured to train a convolutional neural network according to the breast images and the at least one lesion mask, in which the convolutional neural network includes a first branch and a second branch. The first branch is configured to output at least one value to indicate whether a lesion exists. The second branch is configured to output a heat map, and loss values between the heat map and the at least one lesion mask are configured to train the convolutional neural network. The processor is configured to obtain multiple cropped images from the breast images at different levels according to a particular two-dimensional position, and input each of the cropped images into the convolutional neural network to obtain multiple cropped heat maps. The processor is configured to input the cropped heat maps into a recurrent neural network in an order of the levels to obtain multiple output heat maps, combine the output heat maps to obtain a first integrated heat map, and train the recurrent neural network according to loss values between the first integrated heat map and the at least one lesion mask.

In some embodiments, the processor is configured to input multiple negative samples into the convolutional neural network, and retrain the convolutional neural network according to the negative samples that are determined to be positive.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

The using of "first", "second", "third", etc. in the specification should be understood for identifying units or data described by the same terminology, but are not referred to particular order or sequence.

Figure 1:
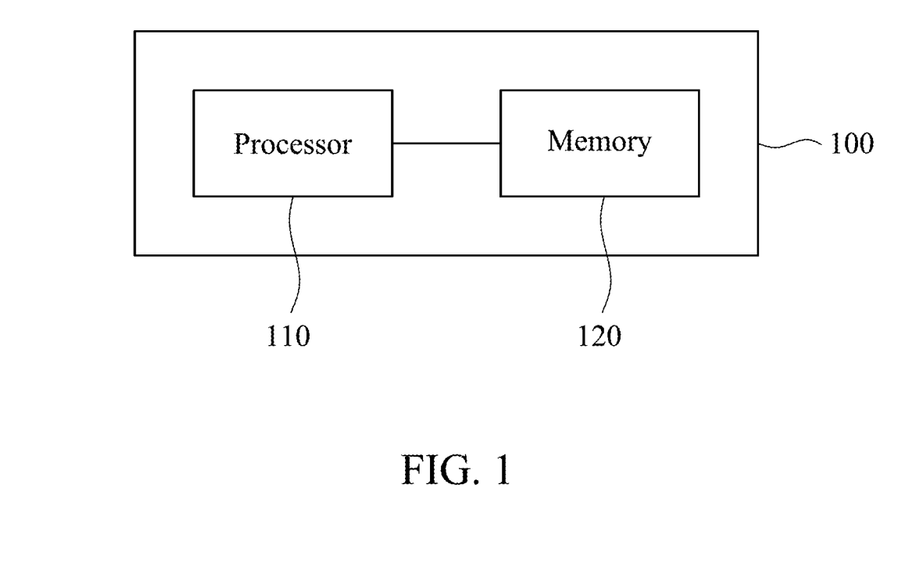
FIG. 1 is a schematic diagram of an electrical device in accordance with an embodiment.

FIG. 1 is a schematic diagram of an electrical device in accordance with an embodiment. Referring to FIG. 1, an electrical device 100 may be medical equipment, a tablet, a personal computer, a notebook computer, a server, a distributed computer, a cloud server, or any electric device having computing ability, which is not limited in the disclosure. The electrical device 100 includes a processor 110 and a memory 120. The processor 110 is communicatively connected to the memory 120 by any wire or wireless communication means or the Internet. The processor 110 may be a central processing unit, a microprocessor, a microcontroller, an image processing chip, an application-specific integrated circuit, etc. The memory 120 may be a random access memory, a read-only memory, a flash memory, floppy disks, hard disks, CD-ROMs, pen drives, tapes, or databases accessible via the Internet. The memory 120 stores instructions that are executed by the processor 110 to perform a method for processing breast tomosynthesis images that will be described in detail below.

Figure 2:
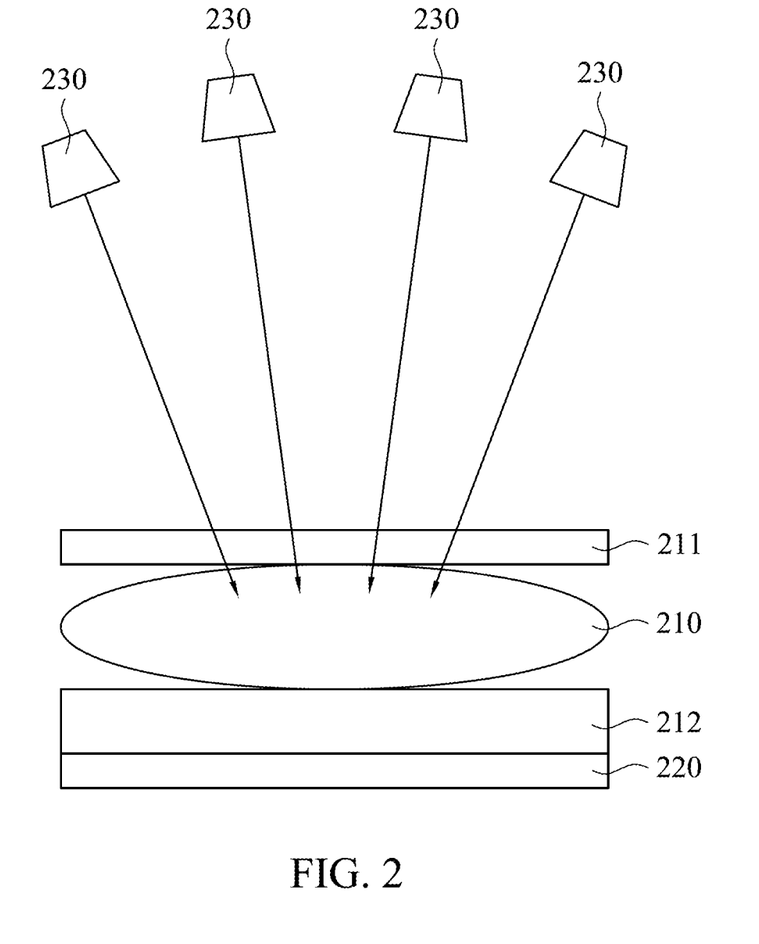
FIG. 2 is a schematic diagram of capturing breast images in accordance with an embodiment.

FIG. 2 is a schematic diagram of capturing breast images in accordance with an embodiment. Referring to FIG. 2, the breast images to be captured are referred to Digital Breast Tomosynthesis (DBT) images. Paddles 211 and 212 are disposed opposite to the each other to fix a breast 210. The breast 210 locates at one side of the paddle 212, and a sensor 220 is disposed at the other side of the paddle 212. An emitter 230 emits X-rays from different angles towards the breast 210. The X-rays penetrate the breast 210 and are received by the sensor 220 to generate the DBT images which can render three-dimensional information. Each of the images can render two-dimensional information, and the information of the third dimension is rendered by multiple levels (e.g. may include dozens of levels). In other words, the third dimension is discretized, and each level is referred to a coordinate at the third dimension. The adjacent levels mentioned below refer to adjacent coordinates in the third dimension. The breast images of the levels may be captured from each angle. In the conventional technology, the breast images of different levels are processed by two-dimensional image processing one by one, but such approach may produce a lot of false positive because there are huge numbers of the images. A novel method is provided which is capable of combining information of different angles and different levels.

Figure 3:
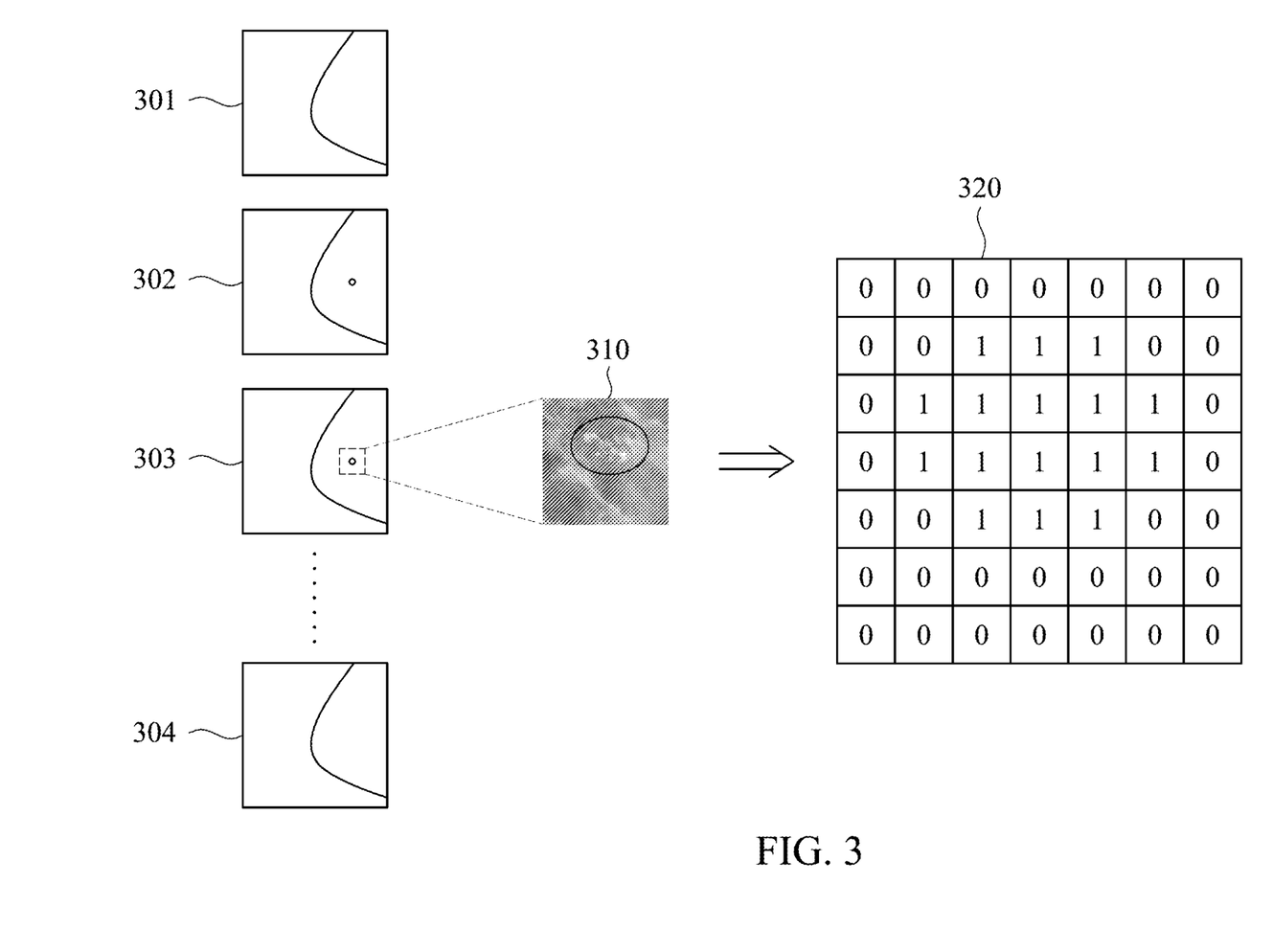
FIG. 3 is a schematic diagram of breast images at different levels and corresponding lesion mask in accordance with an embodiment.

FIG. 3 is a schematic diagram of breast images at different levels and corresponding lesion mask in accordance with an embodiment. Referring to FIG. 3, after the breast images 301-304 at different levels are captured, a lesion (e.g. a tumor) is marked by a doctor who can circle a location where he/she believes the lesion is. An image 310 illustrates a marked portion in the breast image 303. A binarization operation is performed to the marked image 310 to generate a binary image in which, for example, value "1" represents there is a lesion, and the value "0" represents there is no lesion. In some embodiments, the size of the image 310 is 224×224, and therefore the size of the binary image is also 224×224 which may be reduced by a pooling operation as a lesion mask 320 and the size thereof is 7×7 in the embodiment. The lesion mask 320 is used in a machine learning model described below. In some embodiments, the doctor finds the most obvious lesion in the breast image 301-304 and then searches for the lesion in adjacent levels. The lesion in other levels may be used to generate corresponding lesion masks 320. The doctor's marking does not need to be accurate because of the pooling operation. In some conventional technology, the doctor has to segment the lesion from the breast image 303 pixel by pixel, but such approach is too labor-intensive.

Figure 4:
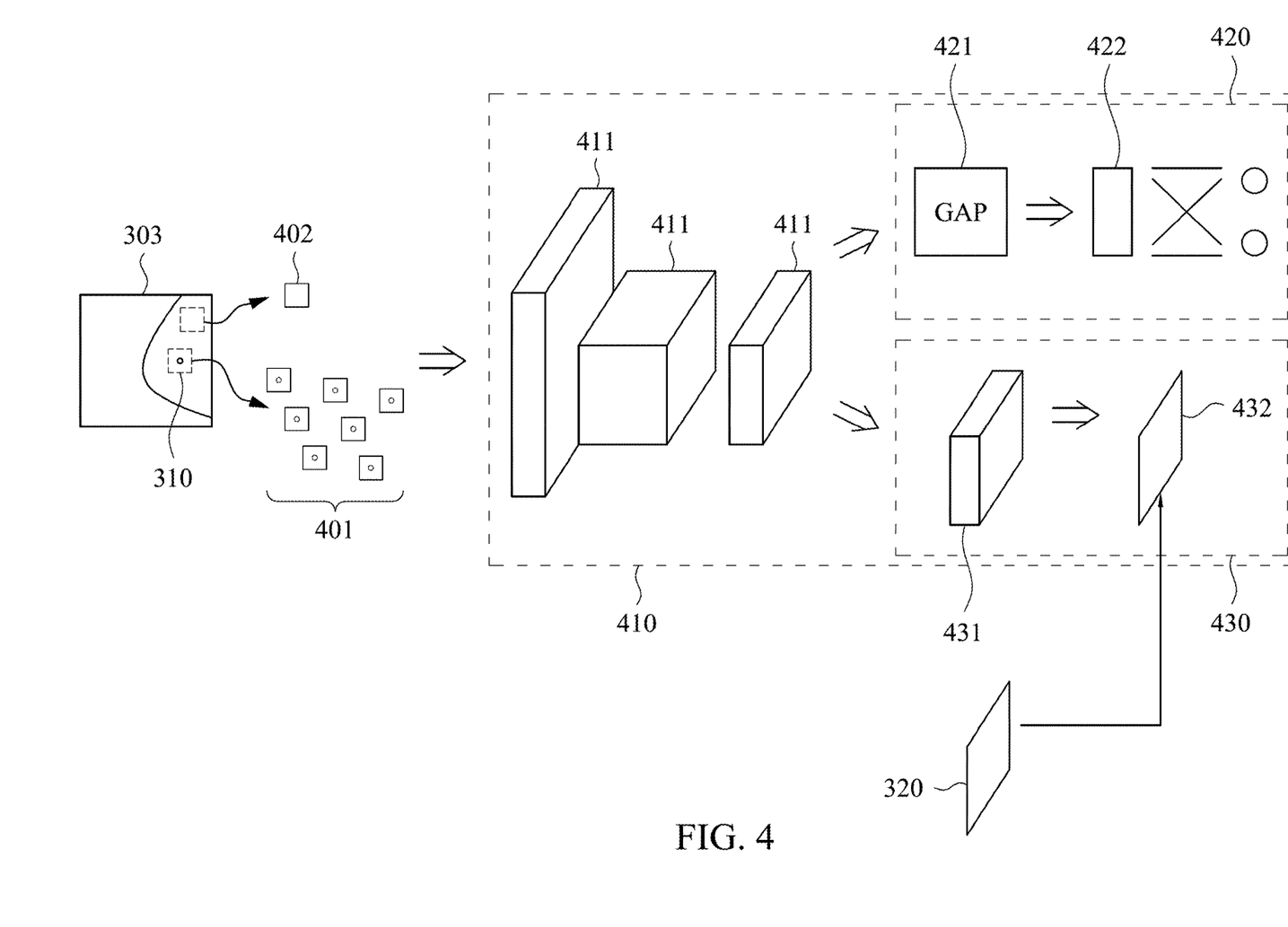
FIG. 4 is a schematic diagram of a convolutional neural network in accordance with an embodiment.

FIG. 4 is a schematic diagram of a convolutional neural network in accordance with an embodiment. Referring to FIG. 4, a convolutional neural network (CNN) 410 is used herein, and the breast image 303 is taken as an example. First, the image 310 where the lesion is marked is extracted from the breast image 303 by a fixed size such as 224×224, but the disclosure is not limited thereto. The image 310 is taken as a positive sample, and other portions of the breast image 303 which are not marked may be chosen arbitrary to generate negative samples 402. Note that the number of the positive sample is way less than the number of the negative samples, and therefore the image 310 may be rotated, shifted or mirrored to produce more positive samples 401. The positive samples 401 and the negative samples 402 are input to the CNN 410 for training.

The CNN 410 includes one or multiple convolution layers 411 (may also include pooling layers), and then is separated into a first branch 420 and a second branch 430. The first branch 420 includes a global average pooling (GAP) layer 421 and a fully connected layer 422 to output two values to indicate whether a lesion exists. For example, one of the values indicate the confidence of positive result (i.e. there is a lesion), and the other value indicate the confidence of negative result (i.e. there is no lesion). In some embodiment, the first branch 420 may output only one value to indicate whether a lesion exists, which is not limited in the disclosure. The second branch 430 includes a convolution layer 431 to output a heat map 432, and the size of the heat map 432 is identical to that of the lesion mask 320. That is to say, the heat map 432 includes 49 values to represent the confidence of the corresponding location where the lesion exists. From another aspect, the first branch 420 is used to determine whether the image has the lesion and heat map output by the second branch 430 is used to point out where the lesion is. Note that the second branch 430 does not include the global average pooling layer and the fully connected layer.

In the training phase, the ground truth for the first branch 420 is set to be value "1" or "0" based on whether the positive sample or the negative sample is being processed. The loss value between the value output by the first branch 420 and the ground truth is calculated. If the positive sample is being processed, the lesion mask 320 generated by the doctor's marking is used; if the negative sample is being processed, the values of the lesion mask 320 represent that there is no lesion (e.g. all the values are zeros). The loss values between the heat map 432 and the lesion mask 320 are calculated for the second branch 430. The loss values may be mean square error or binary cross entropy, which is not limited in the disclosure. The loss values calculated in the first branch 420 and the second branch 430 are used to train the CNN 410. Note that the first branch 420 and the second branch 430 are trained at the same time.

In some embodiments, the CNN 410 is trained by a two-stage approach. To be specific, relatively small amount of negative samples are used in the first stage. In the second stage, multiple negative images (do not have lesion) are obtained, and arbitrary negative samples are extracted from the negative images. The negative samples are input to the CNN 410 produced in the first stage. If the value output by the first branch 420 of the CNN 410 indicates there is lesion, then this sample is a false positive sample. Next, the CNN 410 is re-trained according to the false positive samples.

Figure 5:
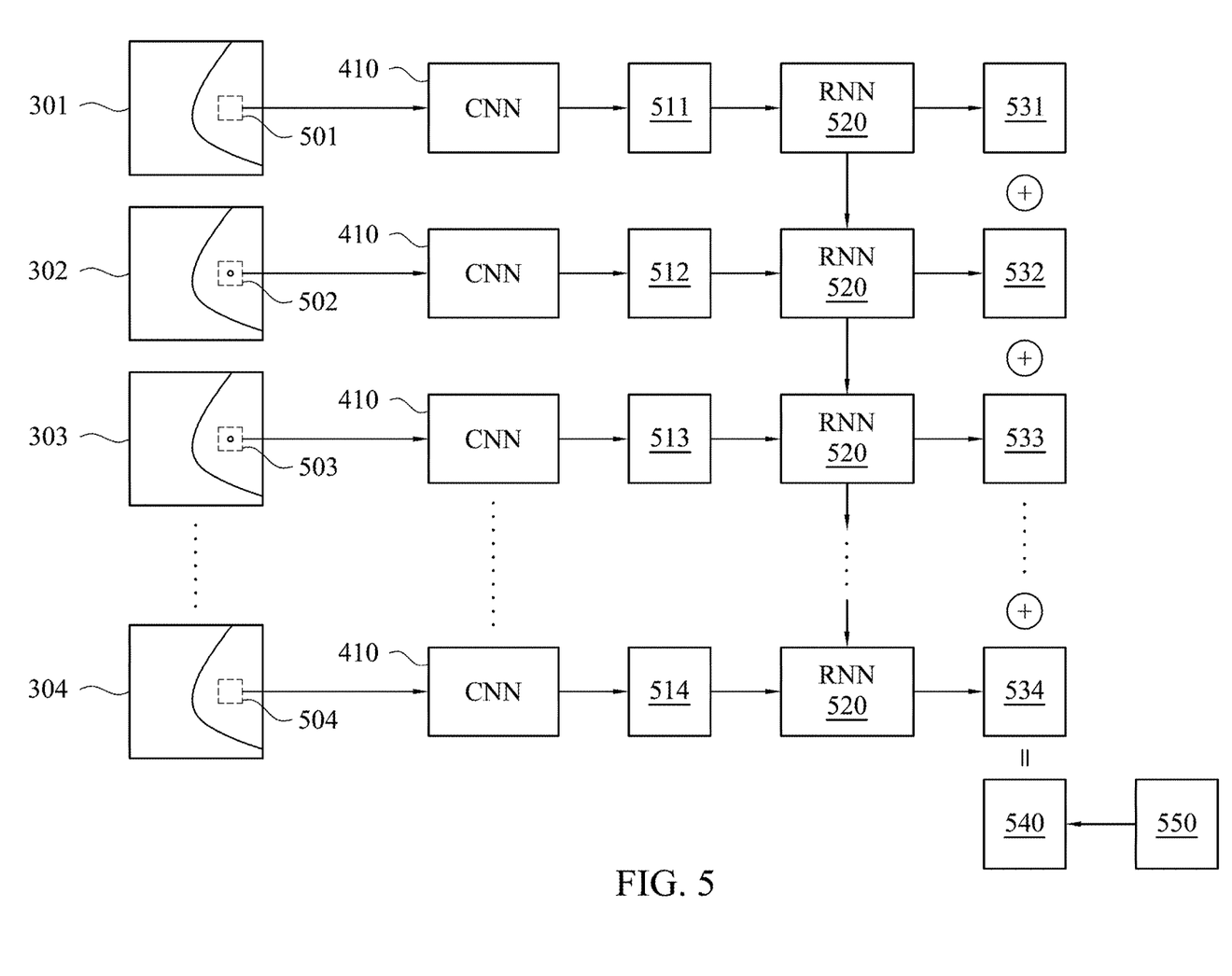
FIG. 5 is a schematic diagram of training a recurrent neural network (RNN) in accordance with an embodiment.

FIG. 5 is a schematic diagram of training a recurrent neural network (RNN) in accordance with an embodiment. Referring to FIG. 5, the breast images 301-304 at different levels are combined herein. In detail, multiple cropped images 501-504 are extracted from the breast images 301-304 according to a particular two-dimensional position. If one of the cropped images 501-504 has a lesion, then the cropped images 501-504 are taken as a positive sample, otherwise is taken as a negative sample. The two-dimensional location of the cropped image 501 in the breast image 301 is identical to that of the cropped image 502 in the breast image 302, and so on. From another aspect, the DBT images are three-dimensional images, the mentioned particular two-dimensional position contains X coordinate and Y coordinate, and the levels are referred to Z coordinate. In the embodiment, the X coordinate and Y coordinate are fixed, and the Z coordinate is changed to obtain the cropped images 501-504. Note that the cropped images 501 and 504 do not have lesions, but the cropped images 502 and 503 have lesions in this example. In some embodiments, if a positive sample is being processed, the cropped images 501-504 may be rotated, shifted or mirrored to produce more positive samples.

Each of the cropped images 501-504 is input to the CNN 410 to obtain corresponding cropped heat maps 511-514 from the second branch 430. In the embodiment, the size of each cropped heat maps 511-514 is 7×7. Next, the cropped heat maps 511-514 are input to a recurrent neural network (RNN) 520 in an order of the levels (from small Z coordinate to great Z coordinate, or from great to small). The RNN 520 is, for example, a Long Short-Term Memory (LSTM) network, but the disclosure is not limited thereto. Each time a cropped heat map is input, the RNN 520 outputs a heat map (also referred to an output heat map). The cropped heat maps 511-514 corresponding to output heat maps 531-534 respectively.

Next, the output heat maps 531-534 are combined to obtain an integrated heat map 540. For example, the average of the output heat maps 531-534 is calculated as the integrated heat map 540. In some embodiments, a maximum value of the output heat maps 531-534 is calculated for each two-dimensional location (total of 7×7 locations), and these maximum values at different locations constitute the integrated heat map 540.

Next, the RNN 520 is trained according to a loss value between the integrated heat map 540 and a lesion mask 550. The loss value may be mean square error or binary cross entropy, which is not limited in the disclosure. When the cropped images 501-504 contain only one marked image (e.g. the marked image 310 of FIG. 3), then the lesion mask 320 is taken as the lesion mask 550. When there are multiple marked images, these marked images may be projected onto a two-dimensional plane (i.e. X-Y plane) of one of the levels, and the marked images are combined by their max value, min value, or by a voting approach. The RNN 520 is configured to extract the relationship between the cropped heat maps 511-514 to achieve higher accuracy. For example, both of the consequent cropped heat maps 502 and 503 have lesions, and therefore the RNN 520 will learn to increase the confidence value when multiple consequent cropped heat maps have lesions.

Referring to FIG. 2, the aforementioned method is applied to one angle (also referred to a first angle), the generated integrated heat map 540 is referred to a first integrated heat map. The same method can be applied to other angles of the breast images (e.g. a second corresponds to a second integrated heat map in which the second angle is different from the first angle). In some embodiments, the integrated heat maps of different angles may be combined to generate a lesion position, for example, by the disclosure of application number U.S. Ser. No. 16/662,049, (U.S. Pat. No. 11,145,056) and the disclosure thereof is taken as a reference herein. In some embodiments, a total of four angles of integrated heat maps are combined, but more or less angles of the integrated heat map may be combined in other embodiments, which are not limited in the disclosure.

The aforementioned disclosure includes at least three technical means. First, the lesion marked is used to calculate the loss value, and the doctor is only required to mark the position (does not need to be very accurate) because the polling operation is applied, and it reduces the time required for marking. Second, the two-stage training is applied to the convolutional neural network, and it can reduce the error rate. Third, the output images from the RNN are combined to generate the integrated heat map before the loss value between the integrated heat map and the lesion mask are calculates, and it can extract the relationship between the breast images of different levels. The influence of these means on sensitivity (SEN) and specificity (SPE) can be referred to the following Table 1.

TABLE 1

| Means | SEN | SPE |
|---|---|---|
| None | 72.4% | 60% |
| + means 1 | 79.3% | 75% |
| + means 1 and 2 | 80.9% | 78.1% |
| + means 1, 2 and 3 | 85.5% | 77.1% |

Figure 6:
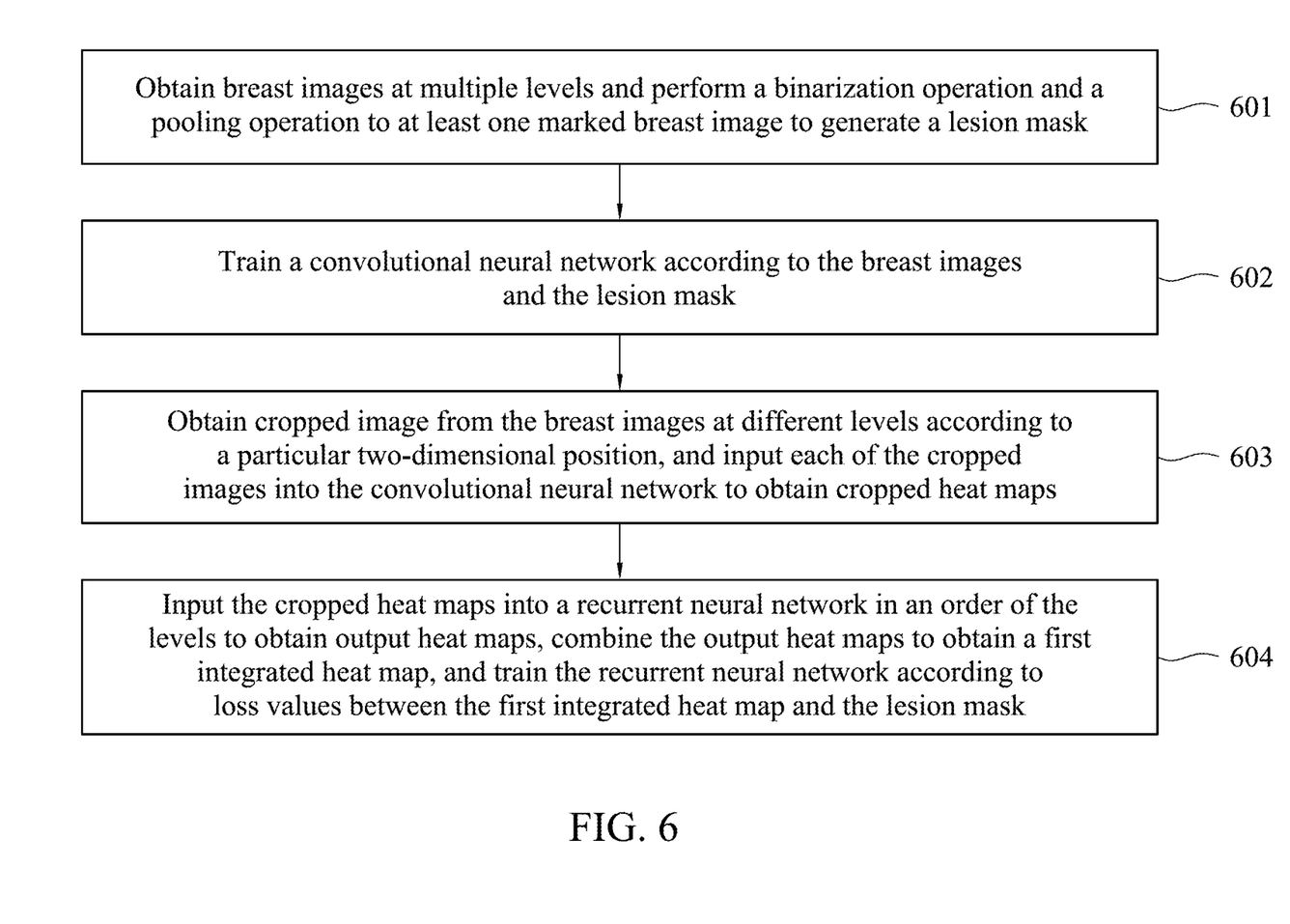
FIG. 6 is a flow chart of a method for processing DBT images in accordance with an embodiment.

FIG. 6 is a flow chart of a method for processing DBT images in accordance with an embodiment. Referring to FIG. 6, in step 601, breast images at multiple levels are obtained, and a binarization operation and a pooling operation are performed to at least one marked breast image to generate a lesion mask. In step 602, a convolutional neural network is trained according to the breast images and the lesion mask. The convolutional neural network includes a first branch and a second branch. The first branch outputs at least one value to indicate whether a lesion exists, and the second branch outputs output a heat map. The loss values between the heat map and the lesion mask are used to train the convolutional neural network. In step 603, multiple cropped image are obtained from the breast images at different levels according to a particular two-dimensional position, and each of the cropped images is input into the convolutional neural network to obtain multiple cropped heat maps. In step 604, the cropped heat maps are input into a recurrent neural network in an order of the levels to obtain multiple output heat maps, the output heat maps are combined to obtain a first integrated heat map, and the recurrent neural network is trained according to the loss values between the first integrated heat map and the lesion mask. However, all the steps in FIG. 6 have been described in detail above, and therefore the description will not be repeated. Note that the steps in FIG. 6 can be implemented as program codes or circuits, and the disclosure is not limited thereto. In addition, the method in FIG. 6 can be performed with the aforementioned embodiments, or can be performed independently. In other words, other steps may be inserted between the steps of the FIG. 6.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method for processing breast tomosynthesis images on an electrical device, the method comprising:
   obtaining a plurality of breast images at a plurality of levels and performing a binarization operation and a pooling operation to at least one marked breast image of the breast images to generate at least one lesion mask, wherein the at least one lesion mask comprises a plurality of values to represent if there is a lesion or not;
   training a convolutional neural network according to the breast images and the at least one lesion mask, wherein the convolutional neural network comprises a first branch and a second branch, the first branch is configured to output at least one value to indicate whether a lesion exists, the second branch is configured to output a heat map, and loss values between the heat map and the at least one lesion mask are configured to train the convolutional neural network;
   obtaining a plurality of cropped images from the breast images at different ones of the levels according to a particular two-dimensional position, and inputting each of the cropped images into the convolutional neural network to obtain a plurality of cropped heat maps; and
   inputting the cropped heat maps into a recurrent neural network in an order of the levels to obtain a plurality of output heat maps, combining the output heat maps to obtain a first integrated heat map, and training the recurrent neural network according to loss values between the first integrated heat map and the at least one lesion mask.

2. The method of claim 1, wherein the convolutional neural network comprises a plurality of first convolution layers, the first branch and the second branch follow the first convolution layers, the first branch comprises a global average pooling layer and a fully connected layer, the second branch comprises a second convolution layer, and the second branch does not comprise the global average pooling layer and the fully connected layer.

3. The method of claim 2, further comprising:
   inputting a plurality of negative samples into the convolutional neural network, and retraining the convolutional neural network according to the negative samples that are determined to be positive.

4. The method of claim 2, wherein the recurrent neural network is a long short-term memory (LSTM) network.

5. The method of claim 2, wherein the first integrated heat map is an average of the output heat maps.

6. The method of claim 1, wherein the first integrated heat map corresponds to a first angle, a second integrated heat map corresponds to a second angle, the method further comprises:
   combining the first integrated heat map and the second integrated heat map to generate a lesion position.

7. An electrical device, comprising:
   a memory storing a plurality of instructions; and
   a processor communicatively connected to the memory and is configured to execute the instructions,
   wherein the processor is configured to obtain a plurality of breast images at a plurality of levels and perform a binarization operation and a pooling operation to at least one marked breast image of the breast images to generate at least one lesion mask, wherein the at least one lesion mask comprises a plurality of values to represent if there is a lesion or not,
   wherein the processor is configured to train a convolutional neural network according to the breast images and the at least one lesion mask, wherein the convolutional neural network comprises a first branch and a second branch, the first branch is configured to output at least one value to indicate whether a lesion exists, the second branch is configured to output a heat map, and loss values between the heat map and the at least one lesion mask are configured to train the convolutional neural network,
   wherein the processor is configured to obtain a plurality of cropped images from the breast images at different levels according to a particular two-dimensional position, and input each of the cropped images into the convolutional neural network to obtain a plurality of cropped heat maps,
   wherein the processor is configured to input the cropped heat maps into a recurrent neural network in an order of the levels to obtain a plurality of output heat maps, combine the output heat maps to obtain a first integrated heat map, and train the recurrent neural network according to loss values between the first integrated heat map and the at least one lesion mask.

8. The electrical device of claim 7, wherein the convolutional neural network comprises a plurality of first convolution layers, the first branch and the second branch follow the first convolution layers, the first branch comprises a global average pooling layer and a fully connected layer, the second branch comprises a second convolution layer, and the second branch does not comprise the global average pooling layer and the fully connected layer.

9. The electrical device of claim 8, wherein the processor is configured to input a plurality of negative samples into the convolutional neural network, and retrain the convolutional neural network according to the negative samples that are determined to be positive.

10. The electrical device of claim 8, wherein the recurrent neural network is a long short-term memory (LSTM) network.

11. The electrical device of claim 8, wherein the first integrated heat map is an average of the output heat maps.

12. The electrical device of claim 7, wherein the first integrated heat map corresponds to a first angle, a second integrated heat map corresponds to a second angle, wherein the processor is configured to combine the first integrated heat map and the second integrated heat map to generate a lesion position.

\* \* \* \* \*